US006274321B1

(12) United States Patent
Blumberg (10) Patent No.: US 6,274,321 B1
(45) Date of Patent: Aug. 14, 2001

(54) HIGH THROUGHPUT FUNCTIONAL SCREENING OF CDNAS

(75) Inventor: Bruce Blumberg, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/454,704

(22) Filed: Dec. 3, 1999

(51) Int. Cl.[7] .............................. C12Q 1/68; C12P 19/34; C07H 21/04; C07H 21/00
(52) U.S. Cl. ........................... 435/6; 435/91.1; 435/91.2; 536/24.3; 536/24.31; 536/24.32; 536/24.33; 536/25.3; 536/25.32
(58) Field of Search ............................ 435/6, 91.2, 91.1; 536/24.3, 24.31, 24.32, 24.33, 25.3, 25.32

(56) References Cited

U.S. PATENT DOCUMENTS

| | | | |
|---|---|---|---|
| 4,675,285 | 6/1987 | Clark et al. ............................... | 435/6 |
| 5,654,150 | 8/1997 | King et al. ............................... | 435/6 |
| 6,030,787 | * 2/2000 | Livak et al. ............................. | 435/6 |
| 6,040,138 | * 3/2000 | Lockhart et al. ........................ | 435/6 |

OTHER PUBLICATIONS

Craig et al., "Plasmid cDNA–directed protein synthesis in a coupled eukaryotic in vitro transcription–translation system", Nucleic Acids Research, vol. 20 (19), pp. 4987–4995, Sep. 1992.*

Kahl et al., "A Multiple–Approach scintillation proximity Assay to Measure the association between ras and Raf", Analytical Biochemistry, vol. 243, pp. 282–283, Mar. 1996.*

Merian Websters Collegiate Dictionary, 10 th edition, 1998, p. 410.*

Blumberg et al., "Organizer–Specific Homeobox Genes in *Xenopus leavis* Embryos" *Science*, 253:194–196 (1991).

Blumberg et al., "Novel retinoic acid receptor ligands in Xenopus embryos" *Proc. Natl. Acad. Sci. USA*, 93:4873–4878 (1996).

Blumberg et al., "BXR, an embryonic orphan nuclear receptor activated by a novel class of endogenous benzoate metabolites" *Genes Dev.*, 12:1269–1277 (1998).

Blumberg et al., "SXR, a novel steroid and xenobiotic–sensing nuclear receptor" *Genes Dev.*, 12:3195–3205 (1998).

Bonaldo et al., Normalization and Subtraction: Two Approaches to Facilitate Gene Discovery *Genome Res.*, 6:791–806 (1996).

Cho et al., "Molecular Nature of Spemann's Organizer: The Role of the Xenopus Homeobox goosecoid" *Cell*, 67:1111–1120 (1991).

Hanselman et al., "A cDNA–dependent scintillation proximity assay for quantifying apolipoprotein A–I." *J. Lipid Res.*, 38:2365–2373 (1997).

Hawley et al., "Disruption of BMP signals in embryonic Xenopus ectoderm leads to direct neural induction" *Genes Dev.*, 9:2923–2935 (1995).

Heim and Tsien, "Engineering green fluorescent protein for improved brightness, longer wavelengths and fluorescence resonance energy transfer" *Curr. Biol.* 6:178–182 (1996).

King et al., "Expression Cloning in the Test Tube" *Science*, 277:973–974 (1997).

Komiya et al., "A Large–Scale in Situ Hybridization System Using an Equalized cDNA Library" *Anal. Biochem.* 254:23–30 (1997).

Li and Evans, "Ligation independent cloning irrespective of restriction site compatibility," *Nucl. Acids Res.*, 25:4165–4166 (1997).

Lustig et al., "Small Pool Expression Screening: Identification of Genes Involved in Cell Cycle Control, Apoptosis, and Early Development" *Meth. Enzymol.*, 283:83–99 (1997).

Maruyama and Sugano, "Oligo–capping: a simple method to replace the cap structure of eukaryotic with oligoribonucleotides" *Gene*, 138:171–174 (1994).

Mitra et al., "Fluorescence resonance energy transfer between blue–emitting and red–shifted excitation derivatives of the green fluorescent protein" *Gene*, 173:13–17 (1996).

Selvin, "Fluorescence resonance energy transfer" *Meth. Enzymol.*, 246:300–345 (1995).

Suzuki et al., "Construction and characterization of a full length–enriched and a 5'–end–enriched cDNA library" *Gene*, 200:149–156 (1997).

* cited by examiner

*Primary Examiner*—W. Gary Jones
*Assistant Examiner*—Arun Chakrabarti
(74) *Attorney, Agent, or Firm*—Campbell & Flores LLP (57) ABSTRACT

Methods for screening cDNAs that express a product interacting with a target molecule. Individual cDNAs are pooled and the cDNA pools are expressed to obtain expression products, for example by coupled in vitro transcription/translation. The interaction of the products with the target molecule is then assayed, for example by scintillation proximity assay (SPA), to identify pools of interest. By selectively re-pooling the cDNAs and repeating the expression and assay steps, individual cDNAs of interest can be rapidly identified. This method is readily automated in a computer-controlled device for high throughput screening. The invention also provides methods of transfecting a cell with a cDNA identified by the screening method to confer a desired property to a cell or identifying cDNAs from a pool of cDNAs by transfection into cells to confer a desired property.

25 Claims, 6 Drawing Sheets

HIGH THROUGHPUT FUNCTIONAL SCREENING OF CDNAS

BACKGROUND OF THE INVENTION

The present invention relates to functional genomics, and more particularly to high throughput screening of cDNAs expressing products that interact with target molecules of interest.

The initial "structural" phases of the various genome projects have made rapid progress in mapping and sequencing genes. In the next phase, "functional genomics" will explore the functions of these newly identified genes, so their gene products can be identified and characterized by their interactions with other molecules. This will allow genes and their products to be understood in the context of their roles in metabolic pathways, cell-signaling and other complex systems.

Previously, such interactions could only be characterized by laborious and technically demanding biochemical purification to identify the protein of interest, followed by amino acid sequencing and cloning of the gene encoding the identified protein.

Recently, the yeast two-hybrid system has been used, but it can be tedious to perform. The system can also result in a high number of false positives, often caused by factors within the yeast cells, which are not easily controlled. Phage-display libraries have also been used with varying degrees of success. Nevertheless, neither method can be used to readily identify cDNAs encoding proteins that interact with a target molecule of interest.

A further difficulty is that manually sifting through large numbers of genes can be an overwhelming task, even when represented by cDNA clones. Moreover, the products of some of the most functionally important genes such as regulatory genes may be in low abundance, have weak interactions or may participate in molecular interactions that are difficult to manipulate in complex mixtures or in vivo. As a result, throughput is low and assay sensitivity is dependent on the strength of the interaction and complexity of the mixture.

Thus, there is a need for rapid and high throughput functional screening of cDNA libraries. The present invention satisfies this need and provides related advantages as well.

SUMMARY OF THE INVENTION

The present invention provides methods for screening cDNA libraries or arrays of known cDNAs to identify individual cDNAs that express a product having an interaction with a target molecule. First, individual cDNAs are pooled and the pools are expressed, for example by using in vitro transcription/translation. The expression products are then assayed for interaction with a selected target molecule, using an assay such as a scintillation proximity assay (SPA). cDNAs associated with expression pools of interest are selectively re-pooled using a different pooling scheme. By repeating the expression and assay steps for the re-pooled cDNAs, an individual cDNA can be rapidly identified.

The screening method is readily automated in a computer-controlled device for high throughput screening, controlled by software for performing the screening method. The invention also provides methods of transfecting a cell with a cDNA identified by the screening method to confer a desired property to a cell.

DETAILED DESCRIPTION OF THE INVENTION

The present invention provides a method for high throughput screening of cDNAs, such as cDNAs from a library or a defined array. By selectively pooling and screening cDNAs—expressing and screening the expression products for interaction with a target molecule—and iteratively re-pooling the cDNAs for further expression and screening, the method rapidly identifies individual cDNAs of interest. As used herein, the term "cDNA of interest" means a cDNA that can express a product that can interact with a target molecule or complex.

Figure 1:
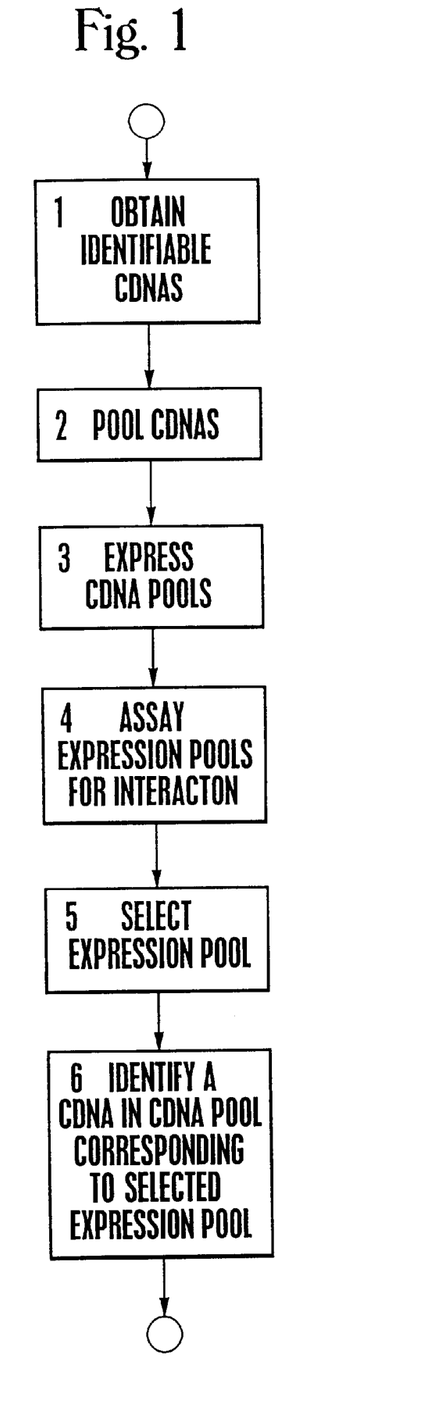
FIG. 1 shows a single iteration of identifying a cDNA in a pool of interest.

As a simplified example for purposes of overview only, FIG. 1 shows a schematic diagram of a single iteration of the identifying steps. The iteration begins by obtaining 1 a number of cDNAs, where the cDNAs are individually identifiable. For example, 96 individual cDNAs can be arrayed on a multiwell plate in a grid of 8 rows (A to H) and 12 columns (1 to 12), forming an arrayed library of individual cDNAs. Thus, the cDNAs can be identified by their positions as A1 to A12, B1 to B12, and so on until H1 to H12. Having an arrayed library is particularly useful for making duplicate plates for subsequent pooling, keeping the individual cDNAs physically separated on the original plate for future reference.

The cDNAs are then pooled 2 according to a preselected pooling scheme. For example, the cDNAs in a daughter plate can be combined down each column into 12 cDNA "column pools" of 8 cDNAs each (A1–H1, A2–H2, A3–H3, etc.). The cDNA pools are then expressed 3 to obtain column pools of expression products, which are representative of the original cDNA column pools. The 12 column expression pools can be identified as A1*–H1*, A2*–H2*, A3*–H3*, etc.

Each of the 12 expression product pools is then assayed 4 for products having an interaction with the target molecule. Based on the results of the assay, column pool A4*–H4* can be selected 5 as containing an expression product, among many, that binds to the target molecule. This allows originating cDNA column pool A4–H4 to be identified 6 as containing at least one cDNA, among others, that expresses a cDNA of interest.

Figure 2A:
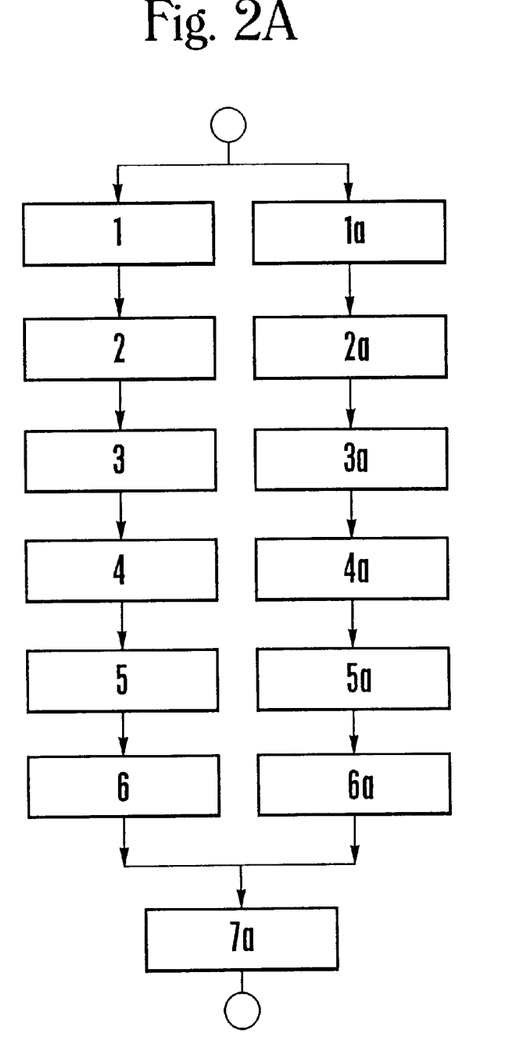
FIGS. 2a, 2b and 2c show examples of the screening method involving multiple iterations of the identification method.

As shown in FIG. 2a, the steps described above 1–6 can then be repeated a second time, using a different pooling scheme than before. During the second iteration, for example, the same 96 cDNAs as before can be obtained 1a from the original source plate by transfer to a second, duplicate daughter plate. The cDNAs are now pooled 2a across each row into 8 cDNA "row pools" of 12 cDNAs each (A1–A12, B1–B12, C1–C12, etc.). As before, the cDNA row pools are expressed 3a to obtain expression row pools (A1*–A12*, etc.), each of which is assayed 4a for interaction with the target molecule. An expression row pool having expression products that interact with the target molecule, such as B1*–B12*, is then selected 5a, allowing the originating a cDNA row pool B1–B12 to be identified 6a.

By comparing the cDNA pools identified in the first and second iterations (A4–H4 and B1–B12), it can be deduced 7a from the pooling scheme that expression product B4* can interact with the target molecule. Accordingly, B4 is a cDNA of interest, which can be readily retrieved in pure form from the original arrayed library. Thus, the cDNA library has been rapidly screened in two iterations to identify a cDNA of interest.

Figure 2B:
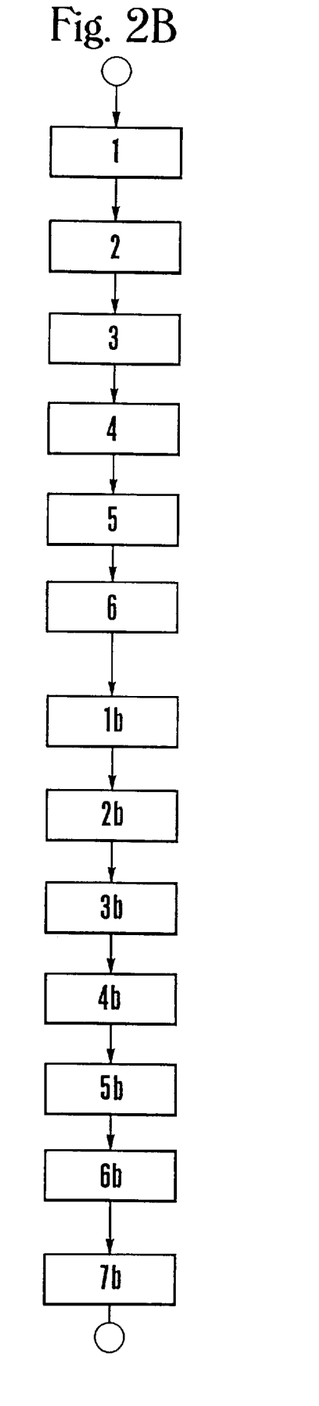

FIG. 2b shows an alternate method where, after performing steps 1–6 in the first iteration, the cDNAs obtained in step 1b are the cDNAs identified in step 6, which are A4, B4, C4, D4, E4, F4, G4 and H4. In step 2b, the 8 individual cDNAs can then be "combined" into "pools" of single cDNAs. Following the steps of expression 3b and assay 4b described above, the expression "pool" that interacts with the target molecule can be selected 5b, rapidly identifying 6b the cDNA B4 as a cDNA of interest 7b.

From this overview, it should be apparent that steps 1–6 in FIG. 1 can be useful for identifying a cDNA in a pool of interest, or serve as a subroutine for repeated iteration. It should also be apparent that the general method is not limited to the 96-well plates used in the overview, but can be performed on many different scales, including screening extremely large numbers of starting cDNAs. Moreover, FIG. 2a shows the subroutine iterated in parallel, so that the cDNAs obtained in steps 1 and 1a are the same cDNAs. It should be noted that the term "parallel" refers to the organization of the iterations without restricting the temporal sequence of the iterations. Thus, the first and second iterations may be performed simultaneously or performed one after another, or a combination of the two. FIG. 2b shows that the subroutine can be iterated in series, where the cDNAs identified 6 in the first iteration are used as the cDNAs obtained 2b for the second iteration. It follows that the subroutine 1–6 can be used in any combination of parallel or series, such as in FIG. 2c, depending on the number of cDNAs to be screened and the physical and time constraints available for performing the method.

The screening method is typically applied to cDNAs and is generally discussed herein in terms of cDNAs. However, the invention is equally applicable to any nucleic acid, whether DNA or RNA, as long as the nucleic acids are individually identifiable and can yield an expression product. For example, the method can be applied to screen genomic DNA libraries or other sources of individual DNAs. The method can also be applied to screen mRNAs, as long as they are individually identifiable. The method can further be applied to screen synthetic libraries of nucleic acids, for example combinatorial libraries. Thus, cDNAs are used as an example of the starting nucleic acids obtained for use in the invention, but the practice of the invention does not depend on the source of the nucleic acids themselves as long as expression products can be obtained.

As used herein, the term "cDNA" means DNA that is complementary to a portion of messenger RNA (MRNA) sequence and is generally synthesized from an mRNA preparation using reverse transcriptase. It should be understood that references to a particular "number" of cDNAs or other nucleic acids actually refers to the number of clones, cDNA sequences or species, rather the number of physical copies of substantially identical sequences present. Moreover, the term is often used to refer to cDNA sequences incorporated into a plasmid, phagemid or other viral vector which can, in turn, be present in a bacterial cell. Thus, when referring to "pooling" of cDNAs, the cDNAs can be manipulated in the form of cells in bacterial colonies.

cDNAs are particularly useful when individually identifiable, whether physically or by an identifier. As discussed above, a particular cDNA can be identifiable by physical location, such as a particular well on a multiwell plate. The format of the identifier is not critical as long as it can be correlated with the particular cDNA. While a particular well may contain more than one cDNA clone, the cDNAs in the well can still be considered identifiable by their well location.

Identifiers can also be used to distinguish individual cDNAs. The identifiers may be unique to each cDNA clone, or may be used to refer to groups of cDNAs having common properties, origins or characteristics. When large numbers of cDNAs or plates are involved, it can be particularly useful to incorporate a computer-readable identifier, such a bar code or magnetic strip, to help automate the pooling process. For example, each clone can be identified by the row and column number of the well in combination with the barcode of the plate. As a result, rather than consisting of a mixture of unknown cDNAs that must be purified later, each pool consists of a defined set of one or more cDNAs that can be identified directly and obtained from the original arrayed library in an isolated form.

For example, cDNAs can be arrayed on one or more multiwell plates by having one clone per well. The clones can be arrayed by hand-picking plated plasmid or phagemid libraries for transfer, or by specialized machines that recognize colonies and transfer them to single wells. The plate can then serve as a source for replication to daughter plates for manipulation, without affecting the original array of cDNAs. If a particular cDNA clone is desired in pure form, it can then be recovered by identifying its original well position.

cDNA libraries are a convenient source for cDNA fragments or full-length cDNAs derived from a particular cell, tissue, organ or organism, whether adult, juvenile or embryonic. cDNA libraries are commercially available from a variety of sources and can also be made using methods known in the art (Blumberg et al. *Science* 253:194–196 (1991); Cho et al. *Cell* 67:1111–1120 (1991); Hawley et al. *Genes Dev.* 9:2923–2935 (1995)).

Libraries enriched for full-length cDNAs are particularly useful because the clones allow initiation from proper transcription initiation sites. Such libraries can be obtained by the oligo-capping method (Maruyama and Sugano, *Gene* 138:171–174 (1994)). This method has been used to obtain libraries with more than 80% full-length clones (Suzuki et al., *Gene* 200:149–156 (1997)). An improved method for producing full-length cDNA libraries is provided in Example IV.

In unamplified cDNA libraries, each clone is unique, reducing the number of clones that must be screened, even for rare cDNAs. Using an unamplified library, 50,000 to 100,000 cDNAs should be sufficient for Drosophila, with 200,000 being a reasonable number for frogs, fish or even mammals.

Normalized libraries are also useful because they reduce the number of abundant mRNAs while increasing the frequency of rare mRNAs. For example, abundant mRNAs can be reduced between 100- to 1000-fold, while rare mRNAs can be increased up to 100-fold. As a result, the number of cDNAs required to be screened is reduced for saturation screening so that an array of 100,000 to 200,000 normalized cDNAs can represent even the rarest mRNAs. Normalized libraries are well known in the art (Soares et al., *Proc. Nat'l*

Acad. Sci. USA 91:9228–9232 (1994); Bonaldo et al., *Genome Res.* 6:791–806 (1996), Komiya et al., *Anal. Biochem.* 254:23–30 (1997)).

A cDNA library is particularly useful when it is in the form of an "arrayed library," which means herein a cDNA library where each clone is separately identifiable. The arrayed cDNA libraries can also be used to produce and reproduce high-density filters for use in traditional screening approaches or can be used to produce very high density arrays on glass slides. The individual cDNAs in the arrayed libraries can also be transfected into cells engineered with reporter constructs to test for in vivo interactions using reporter gene assays.

Once cDNAs are obtained—for example in a cDNA library or more particularly an arrayed cDNA library—one or more of the individual cDNA clones can be combined to form a "pool." While in most cases the pools will contain two or more cDNA clones, a cDNA pool may contain only a single clone, particularly in the later iterations of the screening method or when confirming that a particular cDNA is of interest. Thus, when using an arrayed library, multiple clones can be combined into a single well by hand or by an automated device.

Any scheme of combining at least one cDNA in a mixture can be used. A useful scheme is to organize the cDNAs into a rectangular grid, and pool each row or each column, as described in the overview above. Similarly, the cDNAs can be organized into a three- or higher-dimensional grid, pooling the cDNAs from each plate, or the rows or columns from each plate. Because the wells in the rows, columns and plates are oriented orthogonally, such a pooling scheme can be described as an "orthogonal" scheme. Two or more pooling schemes that are orthogonal to each other can therefore be described as mutually orthogonal.

In variant of the orthogonal scheme, wells that are adjacent or in a predefined zone in a grid can be pooled. For example, in the 8×12 grid discussed in the overview, instead of pooling the columns or rows, the wells can be pooled by adjacent groups of wells such as A1, A2, B1 and B2. Another variant is an overlapping scheme, where an individual cDNA is present in more than one pool for the sake of redundancy. A predetermined level of redundancy ensures that certain cDNAs can be represented by more than one pool, reducing the chances that a cDNA of interest will be missed due to a single assay error. Thus, the particular pooling scheme need not be critical so long as it is predefined and the identity of the individual cDNAs in the pool can be determined.

The number of cDNAs in a pool can be any number such as 96 or 384, which correspond to the number of wells in widely available multiwell plates. The number of cDNAs can also be not about 96 or 100, for example a number greater than 125, such as 192 and 768, 1536 or less than 75 such as 8, 12, 16, 24, 32 or 48. In particular, the number of cDNAs can be 1, so that a single cDNA can be said to be combined for expression and screening, for example in a later iteration of the method.

Once the cDNAs are pooled, they are prepared for expression. High quality DNA from the pools can be obtained in a 96-well format using commercial kits (QIAGEN, Inc., Valencia Calif.) or by well known methods (Itoh et al. *Nucleic Acids Res.*, 25:1315–1316 (1997)). For example, the pooled clones can be grown up in 1 ml cultures using deep well multiwell plates and plasmid minipreps performed on the cultures to obtain DNA ready for expression.

Expression methods useful in the invention should generate expression products for at least a substantial number of the cDNAs present in the pool. One method is to express the cDNAs in vivo in cells such as oocytes or embryos, as described in King et al., *Science* 277:973–974 (1997).

In vitro expression cloning (IVEC) is another useful expression method. IVEC has been previously described (U.S. Pat. No. 5,654,150 to King et al.; King et al., *Science* 277:973–974 (1997); Lustig et al., *Meth. Enzymol.* 283:83–99 (1997)). Unlike previous expression cloning methods, IVEC uses relatively small pools of about 100 cDNAs for transcription and translation in vitro. The use of small pools normalizes the representation of each protein and minimizes sampling bias while simplifying purification of each cDNA.

IVEC uses in vitro transcription/translation (TNT), which has been previously described (Craig et al., *Nucleic Acids Res.*, 20:4987–4995 (1992)) and is commercially available from Promega Corp. (Madison Wis.) and Novagen, Inc. (Madison Wis.). TNT can use a rabbit reticulocyte lysate that has been optimized for in vitro transcription from bacteriophage T7, Sp6 or T3 RNA polymerase promoters coupled with immediate translation of the resulting mRNAs. TNT begins by adding plasmid DNA containing such promoters to the TNT lysate. After incubation, relatively large amounts of protein can be recovered. Microsomes may be added to produce secreted proteins. Other bacterial-coupled transcription/translation protocols are also available (Bujard et al., *Meth. Enzymol.* 155:416–33 (1987); Stueber et al, *EMBO J.* 3:3143–3148 (1984)). If the starting nucleic acids are individual mRNAs, rather than cDNAs or other forms of DNA, then the transcription can be omitted.

Radioactive amino acids can be used with TNT to obtain radiolabeled proteins, such as with $^{35}S$, $^{125}I$, $^{14}C$ and $^3H$. Another method of detectably labeling the proteins is selenium-methionine labeling or biotinylation. Such labeling can facilitate the later steps of the method when the expression pools are assayed for interaction with a preselected target molecule.

The detection assays used in the method should determine whether any gene products in the expression pools have an interaction with a preselected target molecule. As used herein, the term "target molecule" means any preselected molecule of interest. A target molecule can be a protein, polypeptide or peptide. For example, the target molecule can be an antibody that specifically binds a protein of interest or a lectin that binds a carbohydrate or a glycoprotein of interest. The target molecule can also be a monomer or subunit of a proposed multimeric complex.

Other target molecules include nucleic acids, carbohydrates and lipids. Small molecules can also be a target molecule, such as a drug or metabolite, for example a steroid or retinoid such as 14-hydroxy-retroretinol (14HRR) and anhydroretinol (AR). Other small molecules include vitamins, such as vitamin E and K.

A target molecule can also be any complex of two or more of the components above, for example a complex of individual proteins or protein subunits, a protein:nucleic acid complex, a protein:carbohydrate complex or a protein:small molecule complex. The target molecule can also be any receptor molecule, corresponding ligand molecule, or the bound combination of the two or more.

A particular interaction detected by the assay is binding of an expression product to the target molecule, whether specific, nonspecific, transient, catalytic, reversibly or irreversibly. The interaction can also be an indirect interaction via binding or catalysis of an intermediate molecule such as a cofactor associated with the target molecule.

Scintillation proximity assay (SPA) is a particularly useful assay for detecting an interaction with the target molecule. SPA is widely used in the pharmaceutical industry and has been described (Hanselman et al., *J. Lipid Res.* 38:2365–2373 (1997); Kahl et al., Anal. Biochem. 243:282–283 (1996); Undenfriend et al., *Anal. Biochem.* 161:494–500 (1987)). One commercially available system uses FLASHPLATE scintillant-coated plates (NEN Life Science Products, Boston Mass.)).

The target molecule can be bound to the scintillator plates by a variety of well known means. Scintillant plates are available that are derivatized to bind to fusion proteins such as GST, His6 or Flag fusion proteins. Where the target molecule is a protein complex or a multimer, one protein or subunit can be attached to the plate first, then the other components of the complex added later under binding conditions, resulting in a bound complex.

Oligonucleotides can be synthesized with biotin on the 5'- or 3'-end and bound to streptavidin-coated plates. This is particularly useful for identifying cDNAs expressing enhancer-binding proteins. DNA:protein complexes can be attached as target molecules by first binding the DNA and then adding the protein to the DNA-coated wells under binding conditions, resulting in a bound DNA:protein complex.

Small molecules, which are useful for screening for cellular effectors of small molecules, can be attached to such plates by attaching a linker as long as the linker does not impair its biological properties. Appropriate regions for attachment are known in the literature or can be determined empirically.

Once the target molecule is attached, the expression pool is added, typically in a simple salt and/or detergent solution to maintain the solubility and biological activity of the components. The binding conditions will generally reflect assay conditions for the activity of interest. Thus, other components such as inorganic ions, cofactors and co-enzymes may be added as needed to promote biological interaction between the gene products and the target molecule. Alternatively, binding competitors or specific inhibitors can be added to distinguish between or selectively eliminate different types of binding interactions.

In a typical SPA assay, the gene products in the expression pool will have been radiolabeled and added to the wells, and allowed to interact with the solid phase, which is the immobilized target molecule and scintillant coating in the wells. The assay can be measured immediately or allowed to reach equilibrium. Either way, when a radiolabel becomes sufficiently close to the scintillant coating, it produces a signal detectable by a device such as a TOPCOUNT NXT microplate scintillation counter (Packard BioScience Co., Meriden Conn.). If a radiolabeled expression product binds to the target molecule, the radiolabel remains in proximity to the scintillant long enough to produce a detectable signal.

In contrast, the labeled proteins that do not bind to the target molecule, or bind only briefly, will not remain near the scintillant long enough to produce a signal above background. Any time spent near the scintillant caused by random Brownian motion will also not result in a significant amount of signal. Likewise, residual unincorporated radiolabel used during the expression step may be present, but will not generate significant signal because it will be in solution rather than interacting with the target molecule. These non-binding interactions will therefore cause a certain level of background signal that can be mathematically removed.

If too many signals are obtained, salt or other modifiers can be added directly to the assay plates until the desired specificity is obtained (Nichols et al., *Anal. Biochem.* 257:112–119 (1998)).

Fluorescence resonance energy transfer (FRET) is another useful assay for detecting interaction and has been described previously (Heim et al., *Curr. Biol.* 6:178–182 (1996); Mitra et al., *Gene* 173:13–17 (1996); Selvin et al., *Meth. Enzymol.* 246:300–345 (1995)).

FRET detects the transfer of energy between two fluorescent substances in close proximity, having known excitation and emission wavelengths. As an example, a protein can be expressed as a fusion protein with green fluorescent protein (GFP). When two fluorescent proteins are in proximity, such as when a protein specifically interacts with a target molecule, the resonance energy can be transferred from one excited molecule to the other. As a result, the emission spectrum of the sample shifts, which can be measured by a fluorometer, such as a fMAX multiwell fluorometer (Molecular Devices, Sunnyvale Calif.).

Alternatively, the binding of a fluorescent molecule to another protein often causes its fluorescence to become polarized so that the emission is in a different plane than the fluorescence of the unbound molecules. A normal-and-polarized fluorescence reader is the POLARION fluorescence polarization system (Tecan AG, Hombrechtikon, Switzerland). General multiwell plate readers for other assays are widely available, such as the VERSAMAX reader (Molecular Devices) and the SPECTRAMAX multiwell plate spectrophotometer (Molecular Devices).

Once SPA, FRET or other assay method is used to identify an expression pool containing a gene product of interest, the originating cDNA pool—as well as its individual cDNA clones in the defined array—can be identified for further study. A notable advantage of this method is that identification of the cDNA pools of interest does not require separation or recovery of the labeled expression product from the target molecules. The steps of the first iteration can then be repeated for one or more iterations of pooling, expression and assaying.

Figure 2C:
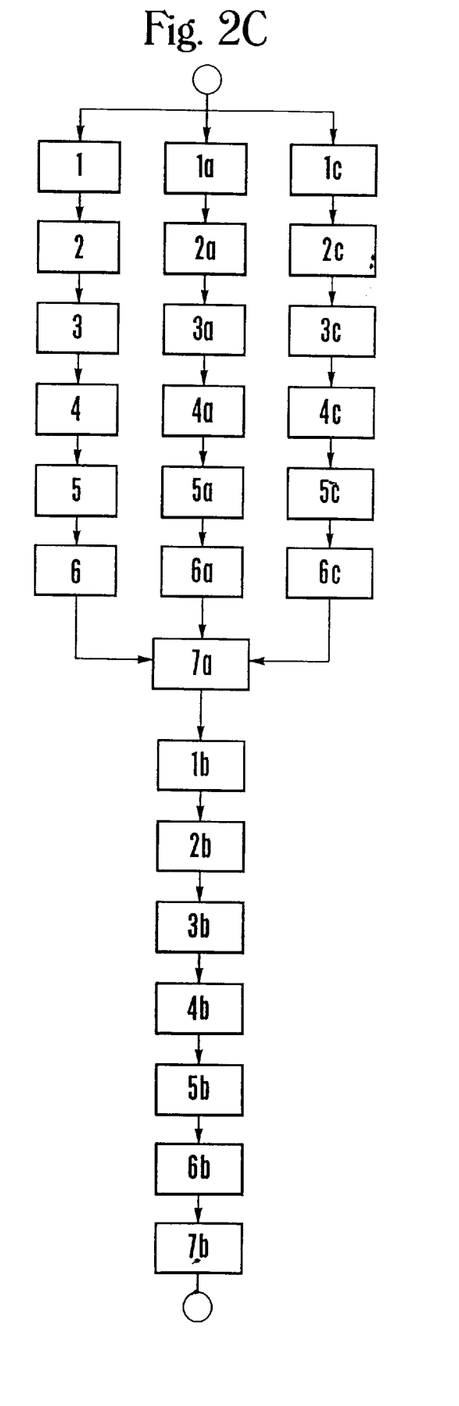

As discussed in the overview above, the steps of obtaining 1, pooling 2 and expressing 3 the cDNAs, then assaying 4 the products to select 5 and identify cDNAs 6, can be repeated in one or more iterations. When the results of the two iterations are compared 7a, the cDNAs of interest can be identified by simple inference or, at the very least, the number of potential cDNAs of interest can be significantly reduced, allowing direct identification in a subsequent iteration.

Where the starting number of cDNAs is large, the method can involve three or more iterations, as shown in FIG. 2c. When screening a library of 9216 individual cDNA species, 24 commercially available plates of 384 wells (16 rows×24 columns each) can be used. In the first iteration, 24 "plate pools" of 384 cDNAs are screened 1–6. In the second iteration, 16 row pools of 576 cDNAs are screened 1a–6a. In the third iteration, 24 "column pools" of 38 cDNA pools identified 7a as fourth iteration, the cDNA pools identified 7a as potentially having cDNA pools of interest are screened as individual "pools" to confirm that they are cDNAs of interest 1b–6b, allowing identification 7b of individual cDNAs of interest.

Alternatively, 16 sets of 24 plates having 384 wells each can be used to screen up to 147,456 clones as follows. Each set of 24 plates are pooled into a single 96-well daughter plate and the pools are screened. Each pool that is a hit from the first iteration is then screened on a single plate of 96 individual clones during the second iteration, allowing rapid identification of cDNAs of interest in two iterations. In another configuration, a 200,000-cDNA library can be arrayed on 520 plates of 384 wells, screened in pools of 96. The pools would occupy 22 plates of 96 wells each, or 6 plates of 384 wells each.

A wide variety of pooling schemes can therefore be used to screen large numbers of cDNAs for a cDNA of interest. If uniform pool size is a priority, the number of pools used in each iteration can be optimized to be the nth root of the starting number of cDNAs, where n is the number of iterations, followed by an optional confirmation iteration. Thus, if a cDNA pool size of 96 is considered optimal, it would possible to screen 9216 species in 96×96-well plates in two iterations, followed by a confirmation iteration.

Once single cDNA clones are identified, they can be sequenced using standard methods, for example by an ABI capillary DNA sequencer 310 (Perkin Elmer Corp., Norwalk Conn.).

As shown above, the method contains iterations of pooling, expression and assay. Thus, the method is especially well suited to automation of one or more of each of steps in the method. For example the device can have computer that controls a means for expressing the cDNA pool to obtain expression products and an automated assay means for determining whether the expression products have an interaction with a target molecule. As used herein, the term "computer" means any CPU-controlled device.

The method described above can be performed by an automated means containing a computer-readable medium carrying a sequence of instructions, where executing the sequence by a processor causes the processor to direct the steps of the method.

The term "automated" as used herein means able to perform the predetermined steps of the method without requiring manual intervention during the process, although manual intervention will typically be required at the beginning and end of the method or at selected points of the method.

The term "computer-readable medium" as used herein refers to any medium that participates in providing instructions to a processor for execution. Such a medium includes non-volatile media, volatile media and transmission media. Non-volatile media includes optical or magnetic media such as a floppy disk, hard disk and CD-ROM. Volatile media includes dynamic memory in the form of RAM, PROM and EPROM and other memory chips. Transmission media includes coaxial cable, metal wire and fiber optics, and can take the form of acoustic or light waves, such as generated during radio and infrared data communications. Computer-readable media also include a carrier wave that carries digital or analog information such as digital data streams or packets.

The term "direct" as used herein means coordination by a central processor to send general instructions to peripheral devices, such as an automated pipetting system or multiwell plate scintillation counter, causing the steps of the method to be performed.

Once a cDNA of interest is identified, it can be used to transfect a cell to confer a desired property to a cell. Methods for transfection in 96-well plates are well known and have been described (Blumberg et al., *Proc. Nat'l Acad. Sci. USA* 93:4873–4878 (1996); Blumberg et al., *Genes Dev.* 12:1269–77 (1998)); Blumberg et al., *Genes Dev.* 12:3195–3205 (1998)). Reporter gene assays can be used to determine the efficiency of transfection, for example using luciferase as the reporter.

Liposomes are a particularly useful method for transfecting cDNA, particularly liposomes containing DOTAP. DOTAP is commercially available from Avanti Polar Lipids (Alabaster Ala.). Prepared DOTAP liposomes are available from Boehringer Mannheim (Indianapolis Ind.).

Lipids useful for making liposomes also include phosphatidylethanolamine (PE), phosphatidyl choline (PC), dioleyloxy phosphatidylethanolamine (DOPE), n-(1-(2,3-dioleyloxy) propyl)-N,N,N-trimethylammonium chloride (DOTMA), dioleoylphosphatidylcholine (DOPC), 2,3-dioleyloxy-N-(2-(sperminecarboxyamido)ethyl)-N,N-dimethyl-1-propanaminium trifluoroacetate (DOSPA), (DOGG), spermine-5-carboxyglycine(N'-stearyl-N'-stearyl) amide tetra-trifluoroacetic acid salt (DOGS), 1,2 dimyristyloxypropyl-3-dimehtyl-hydroxyethyl ammonium bromide (DMRIE), 1,2 dimyristoyl-sn-glycero-3-ethylphosphocholine (EDMPC), 1,2 dioleoyl-sn-glycero-3-ethylphosphocholine (EDOPC), 1 palmitoyl, 2 myristoyl-sn-glycero-3-ethylphosphocholine (EPMPC), dimethyldioctadecylammonium bromide (DDAB), cetyldimethylethylammonium bromide (CDAB), cetyltrimethylethylammonium bromide (CTAB), monooleoylglycerol (MOG), cholesterol, cationic bile salts, spermine-5-carboxyglycine (N'-stearyl-N'-oleyl) amide tetratrifluoroacetic acid salt, spermine-5-carboxyglycine (N'-stearyl-N'-elaidyl) amide tetratrifluoroacetic acid salt, agmatinyl carboxycholesterol acetic acid salt (AG-Chol), spermine-5-carboxy-b-alanine cholesteryl ester tetratrifluoroacetic acid salt (CAS), 2,6-diaminohexanoeyl b-alanine cholesteryl ester bistrifluoroacetic acid salt (CAL), 2,4-diaminobutyroyl b-alanine cholesteryl ester bistrifluoroacetic acid salt (CAB), N,N-bis (3-aminopropyl)-3-aminopropionyl b-alanine cholesteryl ester tristrifluoroacetic acid salt (CASD), (N,N-bis(2-hydroxyethyl)-2-aminoethyl)aminocarboxy cholesteryl ester, carnitine ester lipids, stearyl carnitine ester, myristyl carnitine ester, stearyl stearoyl carnitine ester chloride salt (SSCE), L-stearyl stearoyl carnitine ester (L-SSCE), stearyl oleoyl carnitine ester chloride (SOCE), palmityl palmitoyl carnitine ester chloride (PPCE), myristyl myristoyl carnitine ester chloride (MMCE) and L-myristyl myristoyl carnitine ester chloride (L-MMCE).

Other specific measuring means have discussed in greater detail above, in the examples below, and in the publications and patents cited herein, each of which is hereby incorporated by reference. The following examples are intended to illustrate but not limit the invention.

EXAMPLE I

Manual Screening

The following examples illustrate screening method as can be performed manually.

1. Pooling cDNAs cDNAs are pooled by adding 0.5 μl of bacterial suspension harboring a single cDNA into 1.5 ml of TYE culture medium (15 g bacto tryptone, 10 g yeast extract, 5 g/L NaCl) in a 15 ml tube. A number of innocula are added to the same well, with a typical number of innocula being 96. Alternatively, suspensions can be pooled into 1 ml of TYE medium in 96-well deep well plates having 2 ml capacity per well (Corning-Costar, Corning N.Y.). Bacterial pools are grown and DNA is prepared using conventional methods known in the art for small scale DNA preparation.

If the bacterial polls have been grown in 96-well plates, the following method can be used. The plate is spun for 5 minutes at 3000×g, and the supernatant is decanted. The pellets are resuspended in 25 microliters of solution I (50 mM glucose, 25 mM Tris-HCl pH 8, 10 mM EDTA) and shaken for 5 minutes. Then, 50 microliters of solution II (0.2 N NaOH, 1% SDS) is added. The plate is transferred back to the shaker for 5 minutes of shaking. Then, 160 microliters of solution III (5.3 M guanidine-HCl, 0.7 M potassium acetate, pH 4.8) is added and the plate is shaken for 5 minutes.

A GFB unifilter plate (Fisher Scientific, Pittsburgh Penn.) and a MPBB 25 micron coarse prefilter plate (Fisher Scientific) are rinsed with 100 microliters of phosphate buffered saline (20 mM $NaPO_4$ pH 7.2, 0.15 M NaCl) and aspirated. The GFB plate is placed in the receiving position and the MBPP plate into the filtration position of a UNIVAC vacuum manifold (Whatman Products, Clifton N.J.). Bacterial lysate is added to the MBPP plate. A vacuum is applied until all material is transferred to the receiving plate. The MBPP plate is then discarded. The GFB plate is then transferred to the filtration position and filtered until empty. It is then washed with 0.2 ml 80% ethanol three times and filtered until empty. A 96-well polypropylene V-bottom plate is placed into the receiving position of the manifold. Then 100 microliters of TE (10 mM Tris-HCl pH 8.0, 1 mM EDTA) is added to the GFB plate and filtered by applying vacuum of 2 mm Hg for 5 minutes or until the wells are empty.

2. In vitro Transcription and Translation

In vitro transcription and translation reactions are assembled by adding to a 200 microliter PCR tube the following components: 3.0 microliters of DNA (0.1 mg/ml), 1.8 microliters of $H_2O$, 7.5 microliters of TNT lysate (Promega), 0.3 microliter of bacteriophage RNA polymerase (e.g. bacteriophage T7), 0.3 microliters human placental Rnase inhibitor, 1.2 microliter of $^{35}$S-methionine (New England Nuclear, Boston Mass.), 0.6 microliters TNT buffer (Promega) and 0.3 microliter of 1 mM amino acid mix (minus methionine). The tube is gently mixed and briefly centrifuged. Incubation is for 30 minutes at 30° C.

3. Scintillation Proximity Assay 96-well FlashPlates (New England Nuclear) are incubated for two hours at room temperature with each well containing 150 microliters of a solution of the target to be bound. After incubation, the target solution is removed and the plates rinsed once with 200 microliters of binding buffer, which composition depends on the nature of the target. Methods to determine optimal composition of the binding buffer are well known in the art. Then, 140 microliters of binding buffer are added to each well.

For the SPA assay, an aliquot of labeled protein, typical 10 microliters, is added to each well. After all wells have been filled, the plate is shaken for 1 minute. Incubation is at room temperature for an appropriate period of time, depending on the target.

The readout plate is loaded on a TOPCOUNT NXT microplate scintillation counter (Packard BioScience Co.) to measure binding between the expression product pools and the bound target molecules. In a typical experiment, radioactivity will be counted for 1 minute for each well.

4. Repooling

Pools generating positive signals in the assay are identified. The cDNAs that comprise the original pool are then tested individually for activity.

5. Identification of cDNA

The cDNA responsible for the signal is identified by testing the individual cDNAs from step 3 above.

EXAMPLE II

Automated Screening

The following examples illustrate the screening method as performed by an automated device.

1. Overview of Apparatus

The automated system can be divided into several blocks: a pooling block, an expression block, an assay block, a selection block and an identification block. In addition, the system can also have a transfection block.

Figure 3:
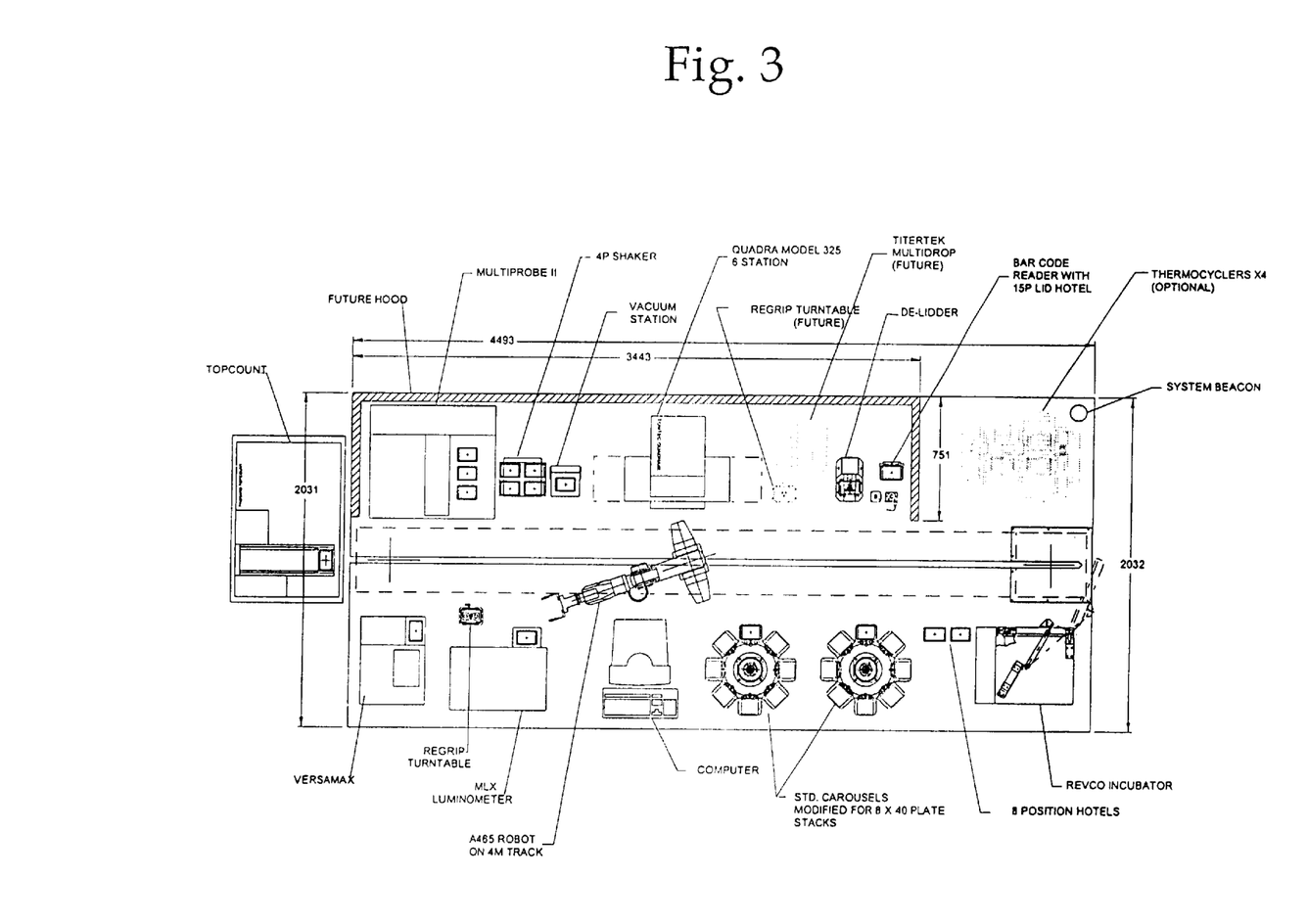
FIG. 3 shows an overhead view of the major hardware components of the automated system.

Each of the blocks is centrally controlled by a PENTIUM-based computer (Dell Computer Corp., Round Rock Tex.) with POLARA software (CRS Robotics Corp., Burlington, Ontario, Canada) running on a WINDOWS NT operating system (Microsoft Corp., Redmond Wash.). Communication and control with the various devices is via network card or RS-232. Plates are transported using an A465 articulated robot arm on a 4-meter linear track (CRS Robotics), arranged as shown in FIG. 3. Unless specified, other hardware components, such as the multiwell plate lid handler, plate turntable, plate carousel and plate hotel rack, are from CRS Robotics Corporation.

2. Pooling Block

The plate pooling block takes an arrayed cDNA library on source plates and pools them on daughter plates.

The plate pooling block starts with up to 384 source plates, which are 94- or 384-well NUNC lidded multiwell plates (Nalge Nunc Int'l, Rochester N.Y.), containing an arrayed cDNA library. There are also 16 daughter plates, which are 96-well deepwell multiwell plates (Corning-Costar), containing 1 ml of TYE media in each well of about 2 ml. Both sets of plates are barcoded and stored in separate plate hotels, which are 25-position hotel racks (CRS Robotics Corp.).

The source and daughter plates are moved to allow access by a QUADRA 96 Model 325 pipetting system (Tomtec, Hamden Conn.). The pipetting system pools 0.5 microliters of clone-containing cells in media from each of the source plate wells to the daughter plate. For 96-well source plates, the transfers are from the same well in each of the source plates to the corresponding well in the daughter plate. For 384-well source plates, the source plate is considered divided into four 96-well quadrants, where each quadrant corresponds to the 96 wells in the daughter plate. The transfer is repeated for each source plate, washing the tips between transfers.

A barcode reader (Microscan, Renton Wash.) also reads the barcodes of the source and daughter plates and stores the information as ASCII files so that each daughter plate has a file that begins with the daughter plate barcode, followed by information about the source plates. The plates are then relidded as necessary and returned to their respective plate hotels.

3. Expression Block a. DNA Filtration Subblock

The DNA filtration subblock isolates DNA from the cDNA pools on the daughter plates and transfers them to a collection plate. The daughter plates are first incubated at 37° C. overnight with continuous shaking in a motorized incubator, for example an INNOVA 4400 incubator (New Brunswick Scientific, Edison N.J.).

After incubation, the plates are removed and transferred to a centrifuge where the bacteria are pelleted. After aspiration of the medium, the plates are replaced into the carousel. The system transfers the plates briefly to the barcode reader to ensure identification and then returns them to the carousel. Barcodes are read for the collection plates, which are 96-well multiwell plates with V-bottom wells (Corning-Costar). Also used are first (MBPP) and second (GFB) sets of filter plates, which are 96-well multiwell filter plates (Polyfiltronics, Rockland Mass.). Again, the daughter, filter and collection plates are initially positioned in the system carousels to allow access by the automated system.

The pipetting system (QUADRA 325) transfers 25 microliters of solution I (50 mM glucose, 25 mM Tris-HCl pH 8, 10 mM EDTA) to the daughter plate. The plate is transferred to the shaker (CRS Robotics) and shaken for 5 minutes to resuspend the bacterial pellets. The plate is returned to the pipetting system, which then adds 50 microliters of solution II (0.2 N NaOH, 1% SDS). The plate is transferred back to the shaker for 5 minutes of shaking. The plate is then returned to the pipetting system and 160 microliters of solution III (5.3 M guanidine HCl, 0.7 M potassium acetate, pH 4.8) is added. The plate is transferred to the shaker for 5 minutes of shaking and then returned to the pipetting system.

The robotic system places the GFB plate into the receiving position of the filtration station (CRS Robotics). The pipetting system transfers the contents of the daughter plate into the MBPP plate and the robotic arm transfers the plate to the filtration station. The daughter plate is then discarded. Vacuum is applied (5 mm Hg) for five minutes and then the MBPP plate is discarded. The GFB plate is moved from the receiving position to the filtration position and vacuum (5 mm Hg) is applied for 5 minutes. The GFB plate is returned to the pipetting system, which adds 200 microliters of 80% ethanol to the plate. The plate is returned to the filtration station and vacuum applied for 1 minute. The plate is returned to the pipetting station and the process repeated for a total of three 80% ethanol washes. After the final wash, the vacuum (5 mm Hg) is applied for one additional minute to dry the plate. The GFB plate is returned to the pipetting system and 100 microliters of TE buffer (10 mM Tris-HCl pH 8.0, 1 mM EDTA) added. The 96-well V-bottom collection plate has its barcode read and is placed into the receiving position. The GFB plate is returned to the filtration position and vacuum (2 mm Hg) is applied for 5 minutes. The GFB plate is then discarded and the 96-well V-bottom plate is returned to the appropriate position on one of the 200 plate system carousels (CRS Robotics).

The previous steps are repeated for each daughter plate until all DNAs have been prepared. At this point, all collection plates will be on the system carousel.

b. DNA Amplification Subblock

The DNA amplification subblock can be used to amplify the DNA in the collection plate by PCR.

A 96-well polypropylene PCR plate (MJ Research, Waltham Mass.) has its barcode read and is moved from the carousel to the MULTIPROBE II liquid handler. The system adds to each well 45 microliters of an amplification cocktail containing the following components: (1×PCR buffer, which is supplied with the enzyme, 0.2 mM dATP, 0.2 mM dCTP, 0.2 mM dGTP, 0.2 mM dTTP, 5 units of thermostable polymerase for PCR such as AmpliTaq Gold (Perkin Elmer) or LA enzyme mix (TaKaRa Inc., Kyoto Japan), 1 microgram standard T3 primer, 1 microgram standard T7 primer or other primers complementary to positions in the vector surrounding the insert). The PCR plate is then transferred to the QUADRA 325 liquid handler, along with one of the daughter plates. The liquid handler transfers 5 microliters from the daughter plate to the PCR plate. The daughter plate is returned to the carousel. The PCR plate is moved to an open position on a 96-well, robot-accessible PCR machine, such as an MJR DNA-engine tetrad. When four plates have been moved to the PCR machine, each is covered with a silicone rubber membrane to prevent evaporation. A typical PCR amplification protocol begins with a 10-minute incubation at 95° C. This is followed by 35 cycles of 95° C. for 30 seconds, 55° C. for 30 seconds and 72° C. for 5 minutes. After 35 cycles are completed, there is an additional 10 minute incubation at 72° C., followed by cooling to room temperature. After DNA amplification, the barcode reader reads the barcodes of the plates, which are returned to the carousels. The PCR products may then be used in the coupled transcription/translation subblock or for another purpose, such as spotting onto filters or glass slides for the purpose of creating cDNA arrays.

c. Transcription/Translation Subblock

The coupled transcription/translation subblock produces radiolabeled protein from the cDNA pools in the collection plate.

The plates containing DNA to be transcribed and translated are loaded in a CRS 200 plate carousel (CRS Robotic Corp.). The pipetting system transfers 0.5 to 5 microliters of DNA to an assay plate, which is a 96-well V-bottomed multiwell plate (Nalge Nunc Int'l). The barcode reader then reads the barcode of the assay plate.

The pipetting system adds up to 14.5 microliters of reagents for transcription/translation, depending on the amount of DNA used. An example reaction for transcribing and translating 4.8 microliters of DNA contains the following: 7.5 microliters of TNT lysate (Promega), 0.3 microliter of bacteriophage RNA polymerase (e.g. bacteriophage T7), 0.3 microliters human placental RNase inhibitor, 1.2 microliter of $^{35}$S-methionine (New England Nuclear), 0.6 microliters TNT buffer (Promega) and 0.3 microliter of 1 mM amino acid mix (minus methionine). The plates are then incubated for about 30 minutes at 30EC in a humidified REVCO incubator (CRS Robotic Corp.).

4. Assay Block

After incubation, the pipetting system transfers an aliquot of the reaction product in each well to a corresponding well in a readout plate, which is a FLASHPLATE scintillant-coated 96-well plate (New England Nuclear). The wells of the flash plate have been precoated with the target protein of interest and contain approximately 100 microliters of a saline and detergent-containing buffer. The composition of this buffer will differ depending on the target to be used. Methods to determine the appropriate composition of the buffer are known in the art.

The readout plate is loaded on a TOPCOUNT NXT microplate scintillation counter (Packard BioScience Co.) to measure binding between the expression product pools and the bound target molecules. In a typical experiment, radioactivity will be counted for 1 minute for each well.

5. Selection Block

The output from the microplate scintillation counter identifies which wells contain expression pools having expression products that bind the target molecule. Binding is determined by dividing the total cpm for each well with an average background value derived from a control plate to which a nonspecific target has been bound. A hit will be empirically defined for each experiment. One example of a hit would be a well that contains three times more radioactivity than the average background well. Another example is a well that contains three standard deviations higher radioactivity than the background wells. Each of these wells, and the expression pools in the wells, can be selected as "hits." If there are a large number of hits, with varying degrees of binding, then the pools with the greatest or greater binding can be selected as the hits.

6. Identification Block

Using the data in the data files, the expression pools selected as "hits" are correlated with the identifiers of the cDNAs originally pooled to obtain the hits.

7. Deduction Block

Wells identified as a "hit" in the first iteration will be tracked by the software. In the next iteration, the cDNAs from the pool that generated this hit will be transferred from the source plates to a second set of daughter plates individually, without pooling. These are then expressed, and assayed as described above. A "hit" will be directly identified with a corresponding cDNA as the result of this second iteration.

EXAMPLE III

Transfection 1. 96-well Transfection Using DOTAP

The following example illustrates transfection using DOTAP liposomes.

Typically, a total of 10 micrograms of plasmid DNA is used per plate. For nuclear receptor transfections, the DNA is usually 1 part receptor expression plasmid, 5 parts reporter and 4 parts CMX-β-gal.

The cells are split and seeded at about $5 \times 10^5$ per plate, depending on the type of cells and the doubling time, but seeding at about 25% of confluency is preferred. For CV-1, a confluent 10 cm dish usually yields eight 96-well plates. Immediately before transfection, the cells are rinsed with PBS and 75 ml of medium is added to each well. Then, 100 ml of sterile PBS is aliquoted to 13 ml polystyrene tubes. The DNA is added to each tube, for example 1 mg of CMX-GAL-hRARα, 5 mg of tk-(MH100)$_4$-luc and 4 mg of CMX-β-gal. The liposomes, 75 ml DOTAP at 1 mg/ml, are added to each tube, and mixed gently and incubated for 5 minutes at room temperature. Then, 7.5 ml of medium is added to each tube, from which 75 ml is added to each well of the plate. The plate is then incubated for at least 2 hours to overnight.

The plates are washed once with PBS or fresh medium. Ligands are then added to the medium, for example containing ultra-stripped FBS. The mixture is incubated for 12 to 48 hours, then rinsed with PBS and aspirated. The cells are then lysed in situ by adding 200 ml of lysis buffer (25 mM Tris-PO$_4$ pH 7.8, 15% glycerol, 2% CHAPS, 1% lecithin, 1% bovine serum albumin, 1 mM dithiothreitol, 8 mM MgCl$_2$, 4 mM EGTA, 0.15 mM PMSF) and incubating at room temperature for 30 minutes. An aliquot of 20 to 40 ml is then transferred to an opaque white luminometer plate and another to a clear plate for β-gal assays. The remainder can be stored at −70° C.

2. Automated Transfection Block

The automated transfection block can be used to transfect a cell with a cDNA of interest or to transfect pooled cDNAs into cells to identify a cDNA of interest.

The plate containing DNAs to be transfected is transferred from the carousel to the pipetting system (QUADRA 325), as is a 96-well V-bottom assay plate. The pipetting system transfers 100 microliters of culture medium (DMEM) to each well of the assay plate. It then transfers an aliquot of DNA from each well of the collection plate to the corresponding wells of the assay plate. The assay plate is then transferred to the Multiprobe II. To each well of the assay plate, the Multiprobe adds 5 microliters of DOTAP liposomes (0.2 mg/ml in liposome buffer 20 mM MES pH 6.2, 154 mM NaCl). The plate is transferred to the shaker and shaken for 1 minute. The plate is then transferred to the Quadra 325 and incubated for up to 10 minutes at room temperature. A plate containing cells to be transfected is transferred to the Quadra 325. Each well contains cells and culture medium (DMEM). The Quadra then transfers 100 microliters of DNA/liposome/DMEM from the V-bottom assay plate to the plate with cells. The cell plate is then transferred to the REVCO incubator at 37° C. with CO$_2$ for 12 to 48 hours.

The results of the transfection can be evaluated as follows. The plate is transferred from the incubator to the Quadra pipetting station, which aspirates the medium. The pipetting system then adds to each well 200 microliters of lysis buffer (25 mM Tris-PO4 pH 7.8, 15% glycerol, 2% CHAPS, 1% lecithin, 1% bovine serum albumin, 1 mM dithiothreitol, 8 mM MgCl$_2$, 4 mM EGTA, 0.15 mM PMSF). The plate is then transferred to the shaker and shaken for 5 minutes.

The pipetting system then transfers an aliquot, typically 20 microliters, of lysate from each well of the cell plate to corresponding wells in a first and second daughter plate, which are 96-well multiwell plates (Corning-Costar).

For the first daughter plate, luciferase assay reagents (20 mM Tricine, 1.07 mM Mg(CO$_3$)$_4$—Mg(OH)$_2$5H$_2$O, 2.67 mM MgSO$_4$.7H$_2$O, 0.2 mM Na$_2$EDTA, 0.5 mM D-luciferin, 0.15 mg/ml coenzyme A, 5 mM dithiothreitol, 0.5 mM ATP) are added to each well. The plate is shaken briefly and then the light output is measured using a microplate luminometer such as a GOLD DIGGER HTS microplate luminometer (Torcon Instruments, Torrance Calif.) and the data is stored with the barcode data file.

For the second daughter plate, β-gal assay reagents (60 mM Na$_2$HPO$_4$, 40 mM NaH$_2$PO$_4$, 10 mM KCl, 1 mM MgCl$_2$, 0.37% 2-mercaptoethanol, 2.6 mg/ml ONPG) are added to each well. After 30 minutes of incubation at 37° C., the plate is read on a VERSAMAX reader (Molecular Devices) and the data is also stored in the barcode data file.

EXAMPLE IV

Synthesis of Normalized, Full-length cDNA Libraries

1. Preparation of mRNA

Freshly collected or frozen embryos are homogenized in 10 volumes of 3M LiCl, 6M urea, 0.1% SDS, and then incubated overnight on ice. After collecting by centrifugation, the RNA is completely resuspended in 3M LiCl and recentrifuged. This process is repeated twice to ensure the removal of DNA and denatured cellular proteins. The RNA is finally collected by centrifugation, resuspended in 0.1% SDS, extracted with phenol:chloroform, precipitated with ethanol, rinsed with 70% ethanol, dried and resuspended in DEPC-treated water. This method can recover very close to the theoretical maximum of 4 μg/embryo for Xenopus. RNA quality is evaluated by denaturing agarose gel electrophoresis. The guanidine thiocyanate/CsCl method can also be used, particularly with tissues having high levels of endogenous RNase (Chirgwin et al., *Biochemistry* 18:5294–5299 (1979)).

Poly A$^+$ RNA is purified using commercially available oligo dT latex (Nippon Roche, Tokyo, Japan) such as OLIGOTEX (QIAGEN). The quality of the poly A$^+$ RNA is evaluated by denaturing agarose gel electrophoresis and northern blotting with probes ranging from 2 to 10 kb in size. Batches of RNA that do not produce sharp bands of the expected size are discarded.

2. Selection of Full-length mRNAs

Populations of mRNAs are enriched using 5' oligo-capping for those mRNAs containing the 5' end as follows. This method of cDNA preparation does not bias against the 3' end of the mRNAs, hence the combination of 5' oligo-capping with the cDNA synthesis methods create a population of cDNAs enriched for full-length copies of mRNAs.

Figure 4:
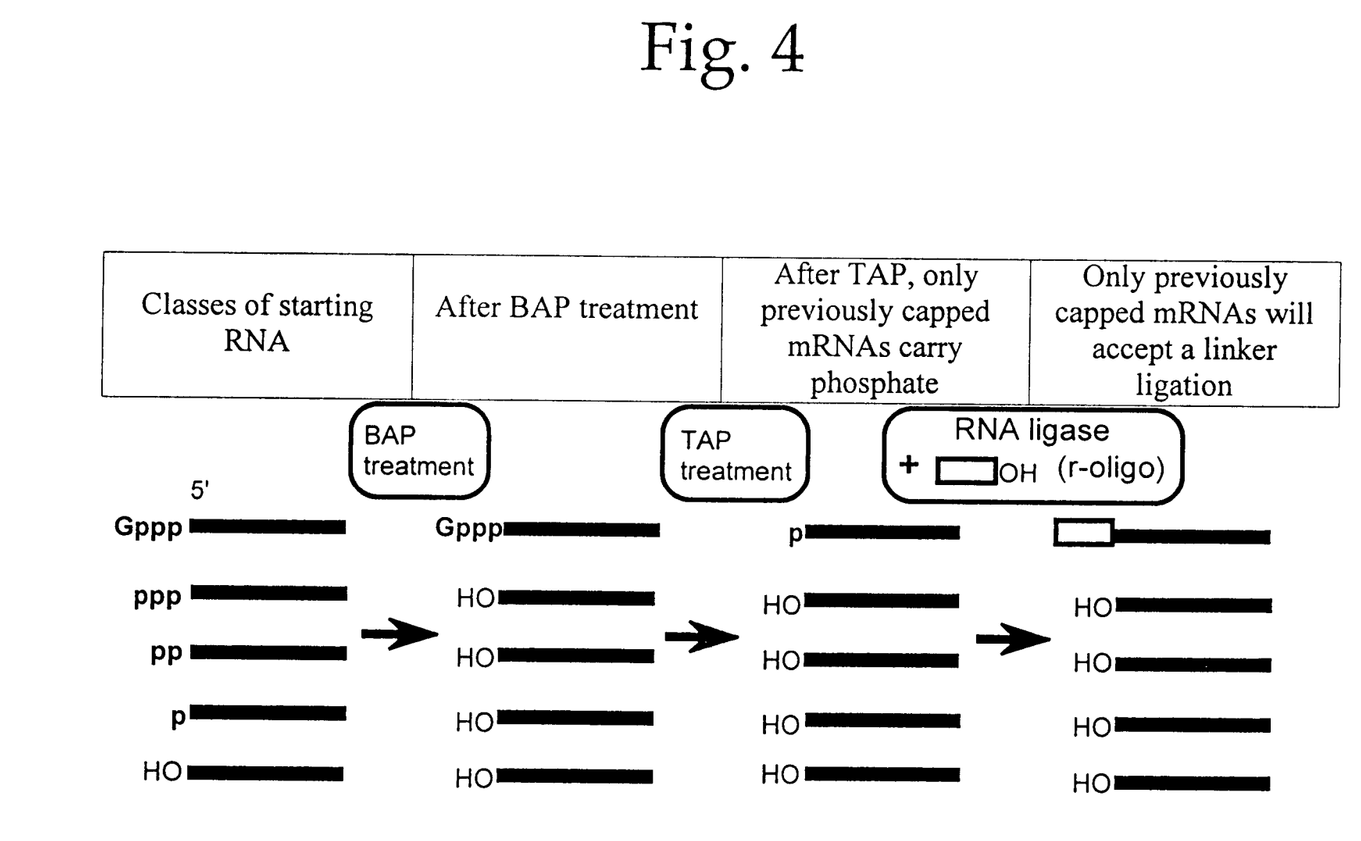
FIG. 4 shows a schematic of the oligo-capping approach to add an oligoribonucleotide to previously capped mRNAs.

Briefly, 5' oligo-capping is a method to add an oligonucleotide to the 5' end of the mRNA:cDNA duplex to identify the 5' end of the cDNA (Maruyama and Sugano, *Gene* 138:171–174 (1994); Suzuki et al., *Gene* 200:149–156 (1997)). The isolated poly A+ mRNA is treated first with bacterial alkaline phosphatase (BAP) to remove the 5' phosphate from any non-capped RNAs. This is followed by treatment with tobacco acid pyrophosphatase (TAP) to remove the cap structure, leaving a 5' $PO_4$ only on previously capped mRNAs (see FIG. 4). These are substrates for adding an unphosphorylated oligoribonucleotide (5'OH-TTTGCAGGATCCCTGCAG; SEQ ID NO:1) with T4 RNA ligase. Thus, only previously capped mRNAs will contain this new 5' sequence. Previous methods use PCR between this 5' primer and a dT-containing primer to select for full-length cDNAs. However, it is likely that any PCR step will alter the representation of cDNAs toward shorter molecules. In this method, the cDNAs are normalized and cloned without PCR amplification, thereby preventing the introduction of a size bias.

3. cDNA Synthesis

Prior to first strand synthesis, the mRNA (typically 5 $\mu$g) is denatured with 15 mM $CH_3HgOH$ (methyl mercury) and incubated for five minutes at room temperature. This is a highly potent nucleic acid denaturant and has been shown to enhance the efficiency of in vitro translation of mRNAs compared with heat denaturation. The methyl mercury is removed by making the mixture 90 mM in 2-mercaptoethanol and incubating for 5 minutes at room temperature. The first strand synthesis reaction contains 5 $\mu$g denatured poly $A^+$ RNA (about 4 pmoles), 50 mM Tris-HCl (pH 8.3 at 55° C.), 10 mM $MgCl_2$, 20 mM KCl, 4 mM sodium pyrophosphate, 2 mM dNTPs, 400 pmoles primer (5'OH-TAGTTCTAGAGGCTCGAG$(T)_{20}$; SEQ ID NO:2), $^{32}$P-dATP (10 $\mu$Ci), 0.6 M trehalose, 100 units human placental ribonuclease inhibitor, and 500 units AMV reverse transcriptase. Incubation is at 55° C. for two hours.

The second strand of the cDNA is made by nick translation of the mRNA:cDNA duplex (Gubler et al., Gene 25:263–269 (1983)) and specific priming with an oligonucleotide complementary to the sequence added during oligo-capping (e.g., 5' OH CTGCAGGGATCCTGCAAA; SEQ ID NO:3). Limited RNase H digestion introduces nicks only into mRNA:cDNA hybrids, and E. coli DNA polymerase I replaces the RNA with DNA. E. coli DNA ligase seals any remaining nicks.

The second strand reaction contains mRNA:cDNA duplexes, 400 picomoles of oligonucleotide, 20 mM Tris-HCl, pH 7.5, 5 mM $MgCl_2$, 10 mM $(NH_4)_2SO_4$, 100 mM KCl, 2.5 units RNase H, 80 units E. coli DNA polymerase I, 0.15 mM $\beta$-NAD and 250 ng E. coli DNA ligase. Incubation is at 14° C. overnight. After second strand synthesis, the cDNA is phenol-extracted, ethanol-precipitated, dried and resuspended in a minimum volume of distilled water.

4. Normalization of the Libraries

Figure 5:
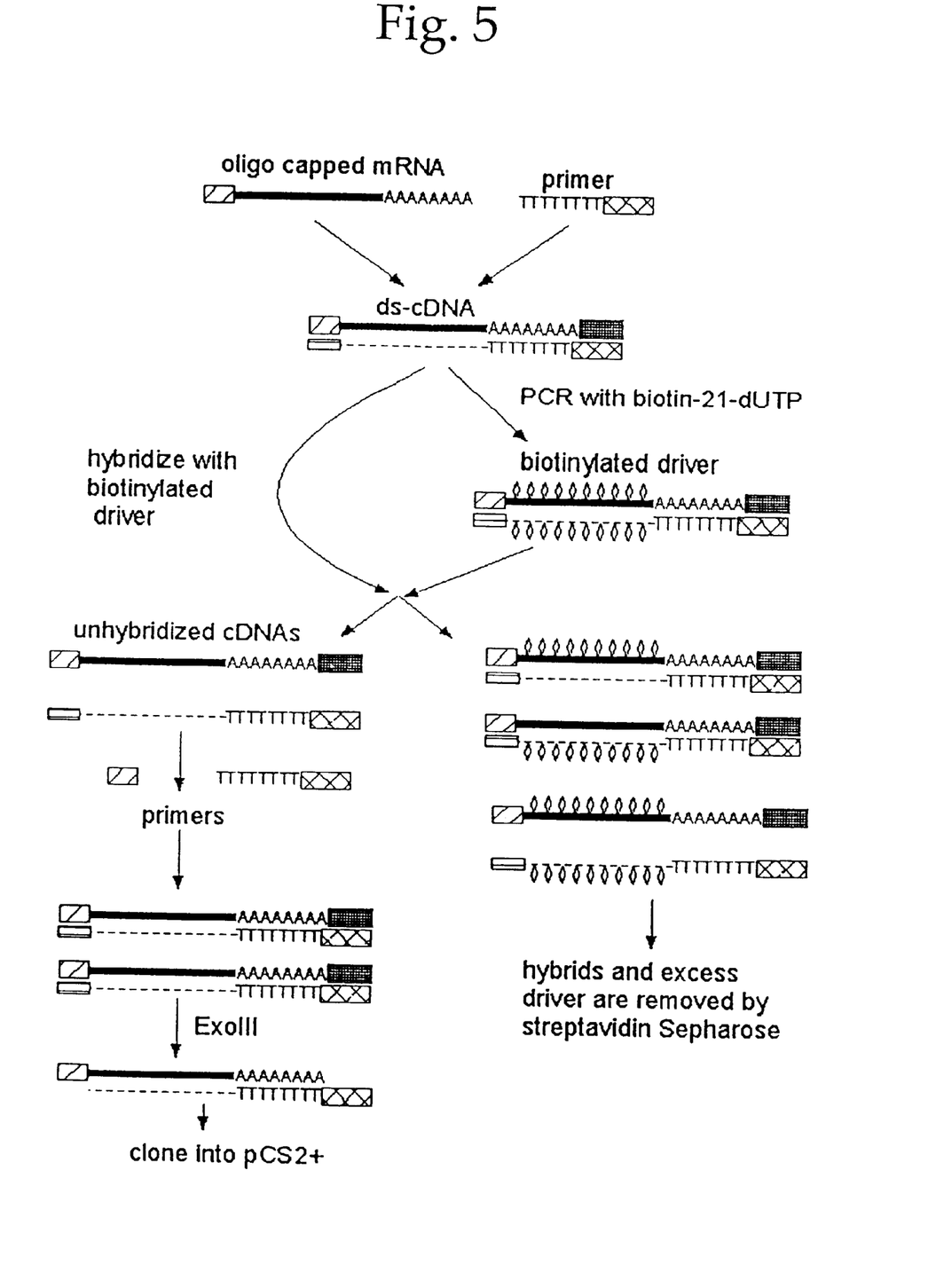
FIG. 5 illustrates a normalization method.

CDNA libraries are normalized as follows. The full-length cDNA population prepared above is used as a template to prepare biotinylated driver for normalization. Biotinylated driver may be prepared by the use of PCR reagents (TaKaRa) in the presence of biotin-21-dUTP using the 5' oligonucleotide 5' OH CTGCAGGGATCCTGCAAA (SEQ ID NO:3) and the 3' oligonucleotide 5'OH-TAGTTCTAGAGGCTCGAG (SEQ ID NO:4) (see FIG. 5). Alternatively, biotinylated primers may be used, omitting the biotin-21-dUTP. The driver is hybridized to the target at 40-fold molar excess to $C_o t=5.5$ (Bonaldo et al., Genome Res. 6:791–806 (1996)). Hybrids and excess driver are removed using streptavidin coupled to a solid support such as SEPHAROSE (Amersham Pharmacia Biotech, Piscataway N.J.) or paramagnetic beads sold by many vendors. The remaining full-length cDNAs are rendered double-stranded by primer extension using the same oligonucleotides and cloned using ExoIII-mediated ligation-independent subcloning as described below.

This method has several potential advantages. First, full-length, capped mRNAs are selected by oligo $d(T)_{30}$ chromatography followed by oligo-capping. PCR is used only to make driver, preventing the introduction of any length bias in the original cDNA population. Finally, after converting the cDNA remaining after subtraction into double stranded molecules, full-length cDNAs are selected for cloning by requiring the 5' and 3' complementary regions to anneal to the vector. The incorporation of biotin into the driver facilitates removal of these hybrids, as well as unbound driver, by simple addition of streptavidin SEPHAROSE beads (Amersham Pharmacia) that strongly bind the biotinylated DNA.

5. Cloning the cDNAs

Figure 6:
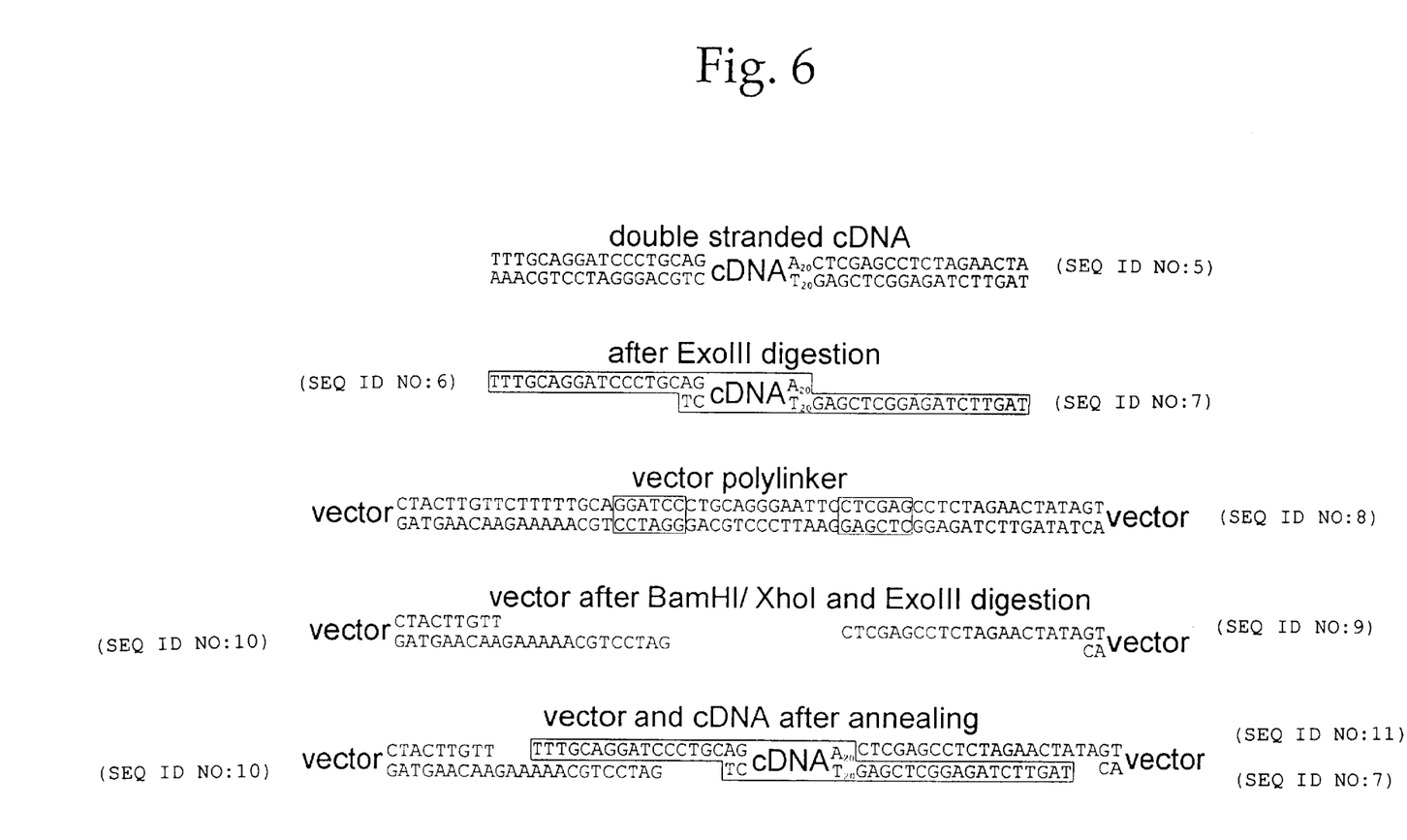
FIG. 6 illustrates Exonuclease III (ExoIII)-mediated ligation-independent cloning.

Exonuclease III (ExoIII)-mediated ligation-independent cloning is used to clone the cDNAs (Li and Evans, Nucl. Acids Res. 25:4165–4166) (see FIG. 6). In this method, primer and linker are used that contain restriction sites and are complementary to an additional 7–10 nucleotides flanking the sites on the 5' and 3' ends. Rather than digesting the cDNA with a restriction enzyme, limited ExoIII digestion exposes the terminal 15–20 nucleotides. Since the insert is not digested with restriction enzymes, there is no need to protect potential internal sites. The vector is digested with the same restriction enzymes contained in the linker and primer (e.g., BamHI and XhoI for pCS2+) and then subjected to limited ExoIII digestion to expose the flanking sequences. The vector and cDNA are annealed and used to transform competent E. coli without the need for ligation. The 15 bp complementary region at each end of the cDNA is sufficient to keep the circles annealed and E. coli repair systems trim overhangs and fill gaps in the plasmid after transformation. ExoIII-mediated ligation-independent cloning also has the advantage that it is impossible to multimerize vectors or inserts since the ends are non-complementary. The only way to form a circle is for one molecule of vector to anneal with one molecule of cDNA. Therefore, it is possible to drive the annealing reaction so that virtually all cDNAs are annealed to a single molecule of vector. The resulting plasmids are electrotransformed into E. coli using methods well known in the art.

Although the invention has been illustrated by the examples above, it should be understood that various modifications can be made without departing from the spirit of the invention. Accordingly, the invention is limited only by the following claims.

We claim:

1. A method of identifying a nucleic acid in a pool of interest, comprising the steps of
   (1) obtaining a plurality of nucleic acids, wherein the nucleic acids are individually identifiable;
   (2) pooling the nucleic acids in step (1) into at least two pools of at least one nucleic acid each;
   (3) expressing the nucleic acid pools in step (2) to obtain corresponding protein expression product pools;
   (4) assaying the expression product pools in step (3) for products having an interaction with a target molecule;
   (5) selecting a nucleic acid pool corresponding to an expression product pool identified in step (4); and
   (6) identifying at least one individual nucleic acid in the nucleic acid pool identified in step (5).

2. A method for functionally screening a plurality of nucleic acids, comprising the steps of
   (a) performing the method of claim 1 on a plurality of nucleic acids using a first pooling scheme;
   (b) performing the method of claim 1 on the nucleic acids at least once using a pooling scheme different than the pooling scheme used in step (a); and
   (c) using the nucleic acids identified in steps (6) of steps (a) and (b) to identify at least one individual nucleic acid;
   thereby screening the plurality of nucleic acids for a nucleic acid that expresses a product that interacts with the target molecule.

3. The method of claim 2, wherein the method of claim 1 in step (b) is performed once.

4. The method of claim 2, wherein the method of claim 1 in step (b) is performed more than once.

5. The method of claim 2, wherein the plurality of nucleic acids obtained in step (1) of step (b) is the plurality of nucleic acids obtained in step (1) of step (a), thereby performing the steps in parallel.

6. The method of claim 2, wherein the plurality of nucleic acids obtained in step (1) of step (b) is the plurality of nucleic acids obtained in step (6) of step (a), thereby performing the steps in serial.

7. The method of claim 2, wherein the pooling schemes are mutually orthogonal.

8. The method of claim 1, wherein the nucleic acid is a cDNA.

9. The method of claim 1, wherein each nucleic acid is associated with an identifier.

10. The method of claim 8, wherein each nucleic acid is physically segregated into an arrayed library.

11. The method of claim 1, wherein the nucleic acids obtained in step (1) are substantially full-length nucleic acids.

12. The method of claim 1, wherein the nucleic acids obtained in step (1) are substantially normalized.

13. The method of claim 1, wherein the nucleic acid pool in step (3) is expressed in vivo in cells.

14. The method of claim 1, wherein the nucleic acid pool in step (3) is expressed using coupled in vitro transcription/translation (TNT).

15. The method of claim 1, wherein the nucleic acid pool in step (3) is expressed to obtain detectably labeled expression products.

16. The method of claim 15, wherein the expression products are radiolabeled.

17. The method of claim 1, wherein the interaction is binding.

18. The method of claim 17, wherein assaying step (4) is performed using a scintillation proximity assay (SPA).

19. The method of claim 17, wherein assaying step (4) is performed using fluorescence resonance energy transfer (FRET).

20. The method of claim 1, wherein steps (2) and (4) are automated.

21. The method of claim 20, wherein step (3) is automated.

22. The method of claim 20, wherein steps (5) and (6) are automated.

23. The method of claim 20, further comprising the step of recording an identifier for each nucleic acid pooled in step (1).

24. The method of claim 20, further comprising the step of recording an identifier for each nucleic acid identified in step (6).

25. A method for conferring a desired property to a cell, comprising the step of transfecting a cell with a nucleic acid identified by the method of claim 2.

* * * * *

SEQUENCE LISTING

<160> NUMBER OF SEQ ID NOS: 14

<210> SEQ ID NO 1
<211> LENGTH: 18
<212> TYPE: DNA
<213> ORGANISM: Artificial Sequence
<220> FEATURE:
<223> OTHER INFORMATION: double stranded cDNA

<400> SEQUENCE: 1
tttgcaggat ccctgcag                                                  18

<210> SEQ ID NO 2
<211> LENGTH: 38
<212> TYPE: DNA
<213> ORGANISM: Artificial Sequence
<220> FEATURE:
<223> OTHER INFORMATION: Primer

<400> SEQUENCE: 2
tagttctaga ggctcgagtt tttttttttt tttttttt                            38

<210> SEQ ID NO 3
<211> LENGTH: 18
<212> TYPE: DNA
<213> ORGANISM: Artificial Sequence
<220> FEATURE:
<223> OTHER INFORMATION: Primer

<400> SEQUENCE: 3
ctgcagggat cctgcaaa                                                  18

<210> SEQ ID NO 4
<211> LENGTH: 18
<212> TYPE: DNA
<213> ORGANISM: Artificial Sequence
<220> FEATURE:
<223> OTHER INFORMATION: Primer

<400> SEQUENCE: 4
tagttctaga ggctcgag                                                  18

<210> SEQ ID NO 5
<211> LENGTH: 18
<212> TYPE: DNA
<213> ORGANISM: Artificial Sequence
<220> FEATURE:
<223> OTHER INFORMATION: double stranded cDNA

<400> SEQUENCE: 5
tttgcaggat ccctgcag                                                  18

<210> SEQ ID NO 6
<211> LENGTH: 18
<212> TYPE: DNA
<213> ORGANISM: Artificial Sequence
<220> FEATURE:
<223> OTHER INFORMATION: cDNA

<400> SEQUENCE: 6
tttgcaggat ccctgcag                                                  18

<210> SEQ ID NO 7
<211> LENGTH: 38

```
<212> TYPE: DNA
<213> ORGANISM: Artificial Sequence
<220> FEATURE:
<223> OTHER INFORMATION: cDNA

<400> SEQUENCE: 7
tttttttttt tttttttttt gagctcggag atcttgat                                38

<210> SEQ ID NO 8
<211> LENGTH: 59
<212> TYPE: DNA
<213> ORGANISM: Artificial Sequence
<220> FEATURE:
<223> OTHER INFORMATION: vector polylinker

<400> SEQUENCE: 8
ctacttgttc tttttgcagg atccctgcag ggaattcctc gagcctctag aactatagt        59

<210> SEQ ID NO 9
<211> LENGTH: 22
<212> TYPE: DNA
<213> ORGANISM: Artificial Sequence
<220> FEATURE:
<223> OTHER INFORMATION: vector polylinker

<400> SEQUENCE: 9
ctcgagcctc tagaactata gt                                                22

<210> SEQ ID NO 10
<211> LENGTH: 23
<212> TYPE: DNA
<213> ORGANISM: Artificial Sequence
<220> FEATURE:
<223> OTHER INFORMATION: vector polylinker

<400> SEQUENCE: 10
gatgaacaag aaaaacgtcc tag                                               23

<210> SEQ ID NO 11
<211> LENGTH: 18
<212> TYPE: DNA
<213> ORGANISM: Artificial Sequence
<220> FEATURE:
<223> OTHER INFORMATION: vector polylinker

<400> SEQUENCE: 11
tttgcaggat ccctgcag                                                     18

<210> SEQ ID NO 12
<211> LENGTH: 38
<212> TYPE: DNA
<213> ORGANISM: Artificial Sequence
<220> FEATURE:
<223> OTHER INFORMATION: double stranded cDNA

<400> SEQUENCE: 12
aaaaaaaaaa aaaaaaaaaa ctcgagcctc tagaacta                               38

<210> SEQ ID NO 13
<211> LENGTH: 20
<212> TYPE: DNA
<213> ORGANISM: Artificial Sequence
<220> FEATURE:
<223> OTHER INFORMATION: cDNA

<400> SEQUENCE: 13
```

```
aaaaaaaaaa aaaaaaaaaa                                                    20

<210> SEQ ID NO 14
<211> LENGTH: 42
<212> TYPE: DNA
<213> ORGANISM: Artificial Sequence
<220> FEATURE:
<223> OTHER INFORMATION: cDNA

<400> SEQUENCE: 14
aaaaaaaaaa aaaaaaaaaa ctcgagcctc tagaactata gt                           42
```